United States Patent [19]

Shiff

[11] 4,068,666
[45] Jan. 17, 1978

[54] SURGICAL SPONGE AND METHOD OF FORMING THE SAME

[75] Inventor: James A. Shiff, Encino, Calif.

[73] Assignee: American Hospital Supply Corporation, Evanston, Ill.

[21] Appl. No.: 578,355

[22] Filed: May 16, 1975

[51] Int. Cl.² .............................................. A61F 13/16
[52] U.S. Cl. .............................. 128/290 W; 128/296; 128/156; 128/290 P
[58] Field of Search ......... 128/296, 290 OB, 290 OR, 128/290 OW, 156, 155, 275, 296; 5/337

[56] References Cited

U.S. PATENT DOCUMENTS

| 3,301,257 | 1/1967 | Crowe et al. | 128/296 |
| 3,638,255 | 2/1972 | Sterrett | 5/337 |
| 3,698,393 | 10/1972 | Stone | 128/296 |

Primary Examiner—Stephen C. Pellegrino
Attorney, Agent, or Firm—Tilton, Fallon, Lungmus & Chestnut

[57] ABSTRACT

A surgical sponge or dressing having an absorbent core enclosed within first and second low-linting porous outer layers. The periphery of the core layer is wrapped within the fold of the reverted edge portion of the first outer layer, and the edge portion of the second outer layer is also reverted and is secured directly to the reverted edge portion of the first layer. The periphery of the core is thereby fully enclosed and the reverted edge portions of the outer layers result in a sponge or dressing having a relatively non-abrasive or atraumatic peripheral construction. The method of forming the improved sponge is also disclosed.

14 Claims, 8 Drawing Figures

SURGICAL SPONGE AND METHOD OF FORMING THE SAME

BACKGROUND

Surgical sponges or pads are commonly used in surgical procedures where body organs and delicate membranes and tissues are exposed. Since exposure to air subjects the body members to radically different environmental conditions than encountered in the moist warmth of the body, it is considered good surgical procedure to simulate an environment more nearly approaching the natural environment. Surgical sponges, moistened with warm saline, are therefore inserted into a body cavity to protect and isolate those organs and tissues not directly involved in the operative procedure. In addition, such sponges or pads are commonly used to absorb surplus body fluids, to serve as aids in grasping and displacing living organs, and to drape exposed organs and tissues to protect them from dehydration.

Conventional surgical sponges are formed of multiple layers of gauze-like material which are unified by lines of machine stitching which extend longitudinally, transversely, or both. Such unification of the multiple layers has been considered necessary to minimize the possibility of separate plies of gauze shifting in position with respect to each other, with the formation of undersirable and possibly trauma-inducing folds and wrinkles, either during use or during laundering and reclaiming. In general, pads made from bleached absorbent gauze have a relatively harsh hand and are not considered suitable for application to delicate body organs without pretreatment. Therefore, it is a common hospital practice to launder such sponges or pads before their initial use to soften the pads and render them less traumatic. Unfortunately, the laundering procedure introduces further disadvantages, since it may tend to create pills of fiber upon the surfaces of the pads. Such pills, if present, must be removed, ordinarily by a combing or picking operation, to avoid or reduce the danger that pills or lint might become detached during use of the pad and, if left within a patient, might produce a foreign body reaction. The laundering procedure might also tend to lubricate the fibrous yarns and thereby free incompletely entrained fibers. Laundering also increases the potential of contaminating the operative incision site by the introduction of residual bleaches, detergents, and other products of the washing process.

Problems in surgical sponge construction are discussed in U.S. Pat. No. 3,678,933, a proposed solution to lint release as disclosed therein consisting of enclosing or encapsulating the exposed fibers in a heat-disintegrated plastic film. Other patents illustrating the state of the art are U.S. Pat. Nos. 3,834,390, 3,837,338, 3,837,344 and 3,837,950.

SUMMARY

This invention is concerned with a disposable single-use non-woven surgical sponge having multiple layers perimetrically connected in relatively non-displacable relation and in such a manner as to provide relatively soft low-linting atraumatic edges. A highly-absorbent core layer, generally formed of fibrous material, is interposed between a pair of substantially lint-free porous outer layers, the outer layers serving as protective barriers against the release of fibers or other particles from the core while at the same time admitting fluids into the pad where they are retained by the absorbent core. The folded periphery of the core is secured within the fold of the reverted or inverted edge portion of one of the outer layers, and the other outer layer having its edge portion similarly reverted and secured to the folded edge portion of the first layer to envelope completely the fibrous absorbent core and to provide a sponge having rounded non-abrasive low-linting edges.

The sponge is fabricated by first superposing the core and porous layers so that one of those porous layers which will ultimately become an outer layer is positioned between the core and the other porous outer layer. The edge portions of all three layers are then secured together, preferably by stitching, along a major part of the total perimeter of the pad, the layers being left unsecured along a minor part of that perimeter. The arrangement of layers is then reversed, or folded inside-out, through the opening or gap defined by the unsecured edges, to revert the edge portions of the outer layers, to fold the edges of the fibrous core within the folded edge portions of one of the outer layers, and to enclose the stitching (which is itself fibrous, potentially abrasive, and a possible source of lint) within the interior of the sponge. The gap is then sewn closed after the edge portion of the outer layers along that gap have been reversely folded. A radiopaque member may be sewn into the sponge prior to the final closing, and a loop or strap may be attached to the externally-stitched portion of the sponge to help in properly orienting the sponge in use and to provide a ready check on the number of sponges during surgery.

Other objects and advantages of the invention will become apparent from the specification and drawings.

DRAWINGS

DESCRIPTION

Figure 1:
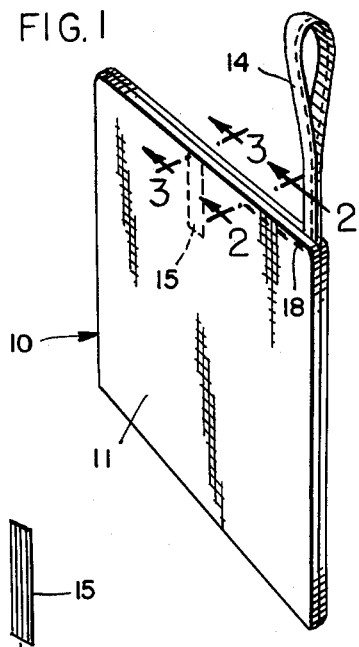
FIG. 1 is a perspective view of a surgical sponge embodying the present invention.

Referring to the drawings, the numeral 10 generally designates a surgical (laparotomy) sponge or pad having a first outer layer 11, a second outer layer 12, and an absorbent core 13. The pad is preferably rectangular (square) in configuration, although other shapes may be used. Size may vary considerably, depending on the type of surgical operation for which the sponge is to be used. Such a sponge may, for example, be as small as 4 or 5 inches, measured along its edge, or as large as 20 inches or more.

The sponge includes a strap or loop 14 and a radiopaque strip 15, both of which are conventional except for the manner in which they are incorporated with the other elements during the fabricating operation. The radiopaque strip 15 may be formed of any suitable non-toxic radiopaque material and simply serves as a means for determining by x-ray examination whether an unaccounted sponge might have been left within a patient. A main purpose of the strap or loop 14 is to provide an external indicator of a sponge that may have been placed within a wound or body cavity to absorb fluids or to isolate or protect an organ. The loop may be formed of any desired material although, in the embodiment illustrated, it is fabricated from the same material as outer layers 11 and 12.

The essential characteristics of the outer layers 11 and 12 are that they be soft, porous, non-linting, strong and durable (even when wet) and, in general, non-irritating both chemically and physically to body organs and tissues. Gauze or other grid materials, if sufficiently soft and non-linting, might conceivably be used. Similarly, conventional woven fabrics or materials might be suitable. Particularly effective results are achieved, however, through the use of porous non-woven materials. For example, outer layers formed of a synthetic (polyester) non-woven material marketed under the designation Nexus 1012 by Burlington Mills, New York, N.Y., have been found highly effective.

The core is formed from any suitable highly-absorbent, usually fibrous, material, either natural or synthetic. Again, particularly effective results have been achieved through the use of hydrophillic non-woven fabrics, one such material being sold under the designation Novonette E9705 by Kendall Company, Wellesley Hills, Mass. Such material is believed to be a non-woven blend of rayon and polyolefin fibers. It is to be understood, however, that other materials having similar properties may be used.

Figure 5:
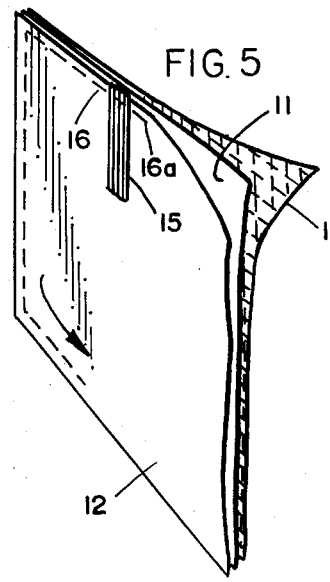
FIG. 5 is a perspective view illustrating the commencement of a second step in the method.
Figure 6:
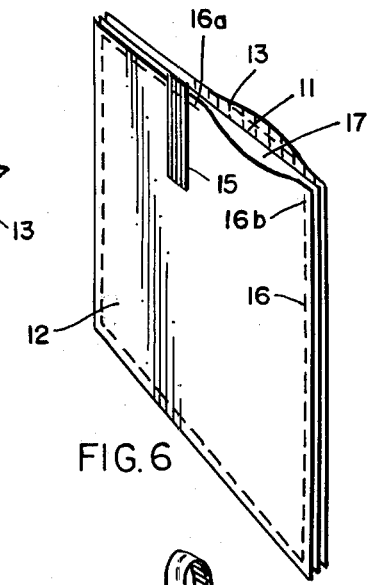
FIG. 6 is a perspective view similar to FIG. 5 and showing completion of the second step.
Figure 7:
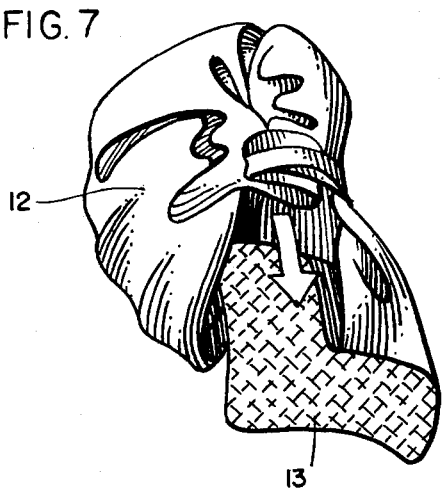
FIG. 7 is a perspective view illustrating a further step of reversely folding the sponge.

FIGS. 4-8 illustrate the sequence of steps in the fabrication of the sponge. It will be noted that the three layers 11-13 are of substantially the same size and are juxtapositioned so that at the commencement of the fabrication operation the first "outer" layer 11 is interposed between outer layer 12 and core 13. The radio opaque strip 15 is conveniently positioned along the exposed surface of layer 12 adjacent one edge thereof and the edge portions of the layers are then secured together along a line of attachment as shown in FIGS. 5 and 6. While such attachment might take the form of adhesive bonding or heat sealing, effective results have been obtained by means of stitching 16. The machine stitching is shown to commence at point 16a intermediate a pair of adjacent corners and to terminate at point 16b adjacent one of those corners; however, the positions of the starting and ending points may be varied as long as the line of stitching extends along a major part of the total perimeter of the juxtapositioned layers. It is essential that a gap or opening 17 be left between layers 11 and 12 since, as shown in FIG. 7, the entire sponge is reversely folded through that gap to reposition the layers as shown most clearly in FIG. 3.

Figure 2:
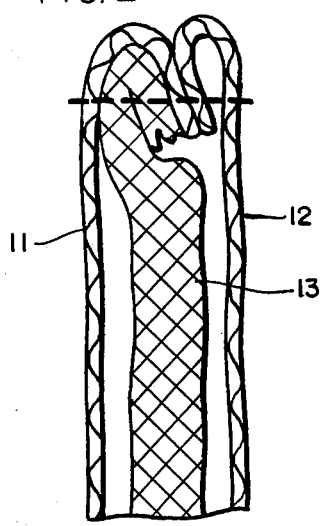
FIG. 2 is an enlarged fragmentary sectional view, presented somewhat schematically for clarity of illustration, taken along line 2—2 of FIG. 1.
Figure 3:
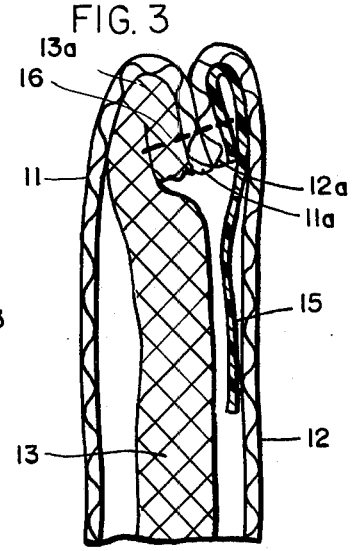
FIG. 3 is a fragmentary perspective view similar to FIG. 2 but taken along line 3—3 of FIG. 1.
Figure 4:
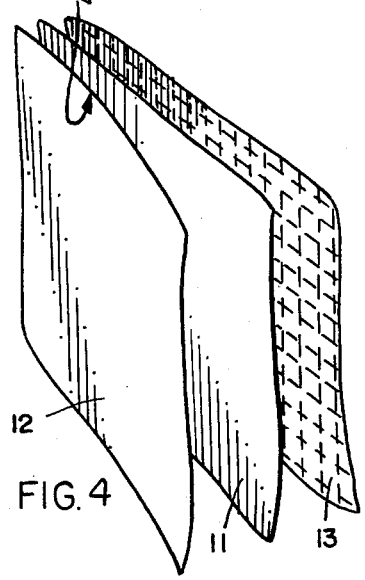
FIG. 4 is a somewhat schematic perspective view illustrating a first step in the method of the present invention.

When such reverse folding is completed, the peripheral edge portions 11a and 12a of porous layers 11 and 12 are reverted or inverted (FIG. 3). Also, the peripheral portion 13a of the absorbent core 13 becomes folded or partially wrapped in the pocket formed by the reverted edge portion 11a of the first outer layer 11. The result is that the core layer, originally oriented as an outside layer, becomes relocated between the porous layers in such a way that the peripheral edge of the core is contained within the fold of one of the outer layers, the two outer layers directly engage each other along the line of stitching to prevent release of core fibers from the sponge, and the edges of the outer layers project inwardly to leave only curved non-abrading surfaces along the outer limits of the sponge. The peripheral portion of the core is itself reverted or folded as shown in FIGS. 2 and 3, so that a mass of material of greater absorbent capacity is concentrated about the sponge's outer limits.

Figure 8:
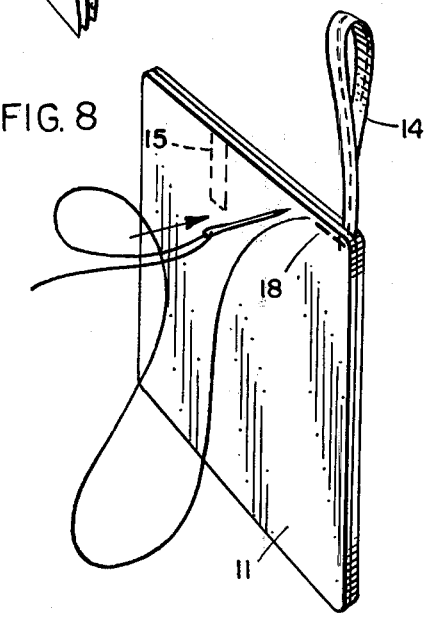
FIG. 8 is a perspective view depicting a final step in the method of forming the sponge.

The final step of sponge fabrication consists of closing the gap between the ends 16a and 16b of stitching 16. The unsecured peripheral portions of the outer layers are reversely turned as shown in FIG. 2 and an additional line of stitching 18 is formed through all of the layers (FIG. 8). Strap or loop 14 may be secured in place by the same externally-formed line of stitching. Since the strap is located along the closed gap, that location aids in properly orienting the sponge so that the exposed stitching which closes that gap would not be introduced into a wound or incision when the strap is used as a sponge counting indicator.

It is to be observed that particularly effective results are obtained where the outer layers are formed from low-linting non-woven materials which are hydrophobic and, because of such hydrophobicity, tend to facilitate the removal of clots which occur during a surgical operation. More specifically, clots which normally occur in and about the operative site tend to cling to the relatively dry outer surfaces of the sponge. The material previously identified by way of example (Nexus 1012) is such a hydrophobic non-woven material.

While in the foregoing I have disclosed an embodiment of the invention in considerable detail for purposes of illustration, it will be understood by those skilled in the art that many of these details may be varied without departing from the spirit and scope of the invention.

I claim:

1. A surgical sponge or dressing comprising an absorbent planar core layer interposed between a pair of porous and substantially non-linting outer layers, said outer layers having reverted peripheral edge portions extending about the entire perimeter of said sponge, said reverted edge portions of the respective outer layers being in contiguous relation with each other and being disposed only on one side of said core layer, said core layer having a reverted peripheral portion received within the fold of the reverted peripheral edge portion of one of said outer layers, and means directly securing the reverted edge portion of said outer layers and the reverted peripheral portion of said core layer together, said core layer having substantial surface portions thereof unsecured to said outer layers.

2. The sponge of claim 1 in which said means comprises stitching extending about the periphery of said sponge.

3. The sponge of claim 2 in which a major part of the length of said stitching is concealed within said sponge.

4. The sponge of claim 1 in which said outer layers are unsecured to each other and to said core layer except along the periphery of said sponge.

5. The sponge of claim 1 in which said layers are of substantially the same peripheral dimensions.

6. The sponge of claim 1 in which said sponge is generally rectangular in shape.

7. The sponge of claim 1 in which said outer layers are formed of porous non-woven material.

8. The sponge of claim 1 in which said core layer is fibrous.

9. The sponge of claim 8 in which said core layer is formed of a matrix of non-woven fibers.

10. The sponge of claim 1 in which said outer layers are formed of non-woven porous hydrophobic material.

11. A method of making surgical sponge or dressing having an absorbent core disposed between first and second porous outer layers, comprising the steps of arranging said core and said outer layers, all of substantially the same planar dimensions, in juxtaposition to form an arrangement wherein said first outer layer is disposed between said core and said second outer layer and all of said layers are unsecured to each other; then securing the edge portions of all three layers together along a major part of the total perimeter thereof while leaving said outer layers unsecured along a minor part of said total perimeter; then reverse folding said layers through the gap defined by the unsecured outer layers to position said outer layers on opposite sides of said core, thereby reverting the edge portions of said outer layers and folding the edge portion of said fibrous core within the fold defined by the reverted edge portion of said first outer layer; and subsequently joining said layers together to close said gap.

12. The method of claim 11 in which said layers are secured together by stitching.

13. The method of claim 11 in which said absorbent core is fibrous.

14. The method of claim 11 in which said outer layers are formed of porous hydrophobic material.

* * * * *